United States Patent [19]

Konopasek

[11] 3,983,476

[45] Sept. 28, 1976

[54] DEFIBRILLATOR TESTING DEVICE

[76] Inventor: Francis Konopasek, 151 Marine Drive, Rottingdean, England

[22] Filed: June 28, 1974

[21] Appl. No.: 484,124

[52] U.S. Cl............................ 324/111; 128/419 D; 324/115; 324/132
[51] Int. Cl.²................. G01R 15/08; G01R 15/10
[58] Field of Search .......... 324/111, 132, 142, 115; 128/419 D, 419 R

[56] References Cited
UNITED STATES PATENTS

| | | | |
|---|---|---|---|
| 3,281,689 | 10/1966 | Schneider et al. | 324/132 |
| 3,747,605 | 7/1973 | Cook | 128/419 D |
| 3,782,389 | 1/1974 | Bell | 128/419 D |
| 3,787,767 | 1/1974 | Hammer et al. | 128/419 D |
| 3,798,542 | 3/1974 | Dempsey | 324/111 |
| 3,865,028 | 1/1975 | Thakore | 324/111 |

OTHER PUBLICATIONS

Cook et al; J. Assn. Advan. Med. Instrum.; 6: 325–329; 1972.

*Primary Examiner*—R. V. Rolinec
*Assistant Examiner*—Ernest F. Karlsen
*Attorney, Agent, or Firm*—Stanley G. Ade

[57] ABSTRACT

The tester does not require any external power source as it derives its energy from the pulse being measured. It includes circuitry which produces a signal proportional to the energy without directly calculating the energy. This is accomplished by generating a current portional to $E^2$ with a diode network and then integrating the current in a capacitor thus indirectly measuring the true energy. The results are read directly upon a linear meter or can be connected to an oscilloscope or the like for inspection or recording. A bridge rectifier can be used so that the circuit is responsive to both polarities of input pulse or it can be made responsive only to the unipolar signal.

4 Claims, 4 Drawing Figures

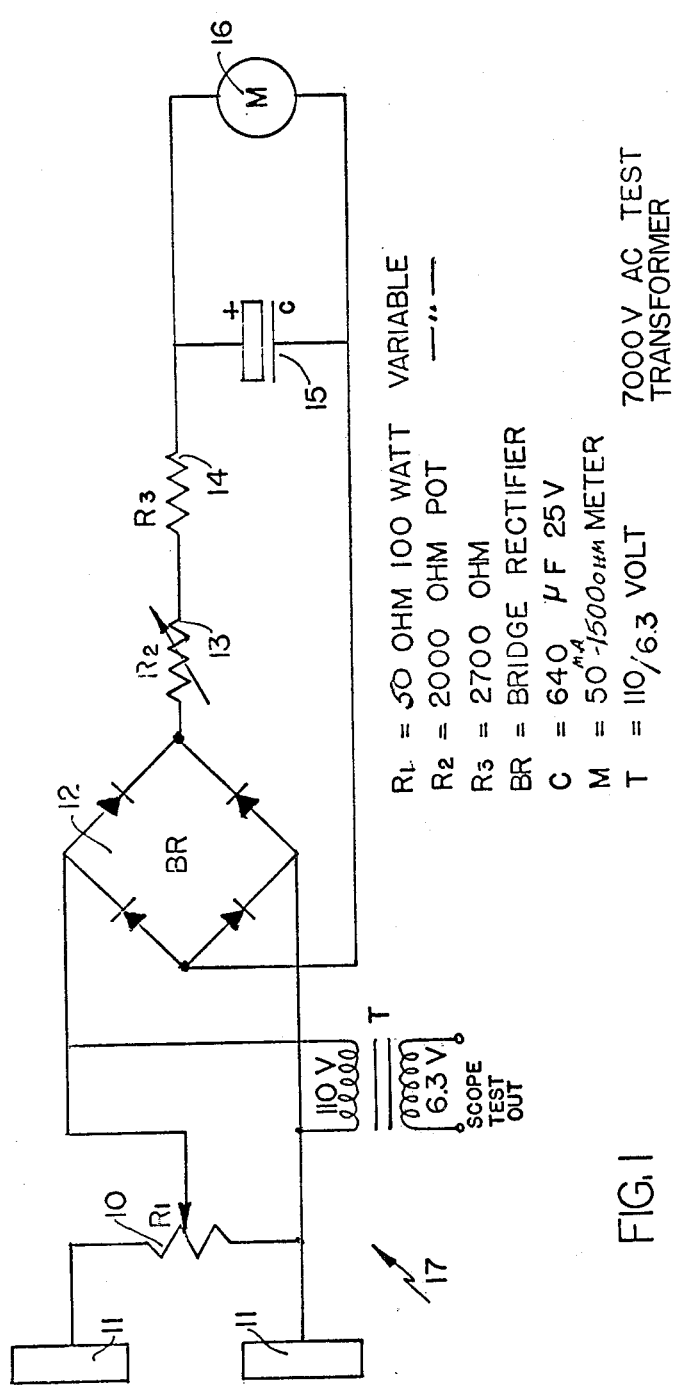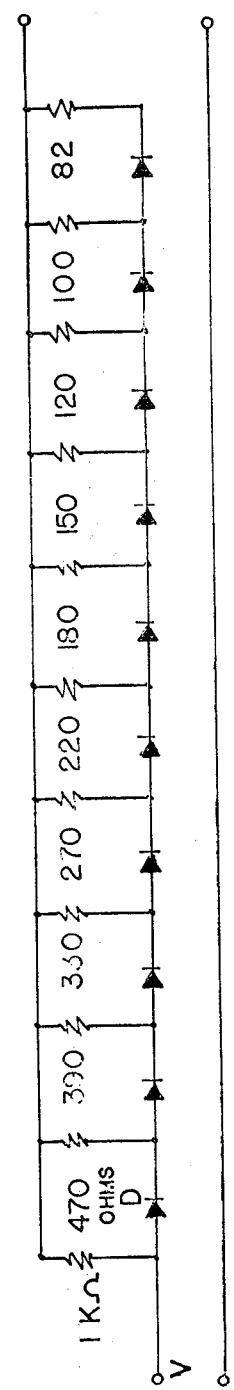

R₁ = 50 OHMS
R₂ =
R₂A =
R₃ = 1 OHM TAPPED
D = GERMANIUM DIODE

DEFIBRILLATOR TESTING DEVICE

BACKGROUND OF THE INVENTION

This application relates to new and useful improvements in methods and apparatus for testing and calibrating D.C. defibrillators.

It is standard practice to measure the energy output of a defibrillator discharged into a standard 50 ohm resistance. This has been done by measuring the voltage and current or just the voltage across the standard test resistance and then calculating energy from the relationship.

$$\text{Energy} = \int EI\, dt \text{ or } \int \frac{E^2}{R} dt.$$

Historically, these measurements were made by the use of oscilloscopes which were photographed, and measurements and calculations were then performed manually or by means of a calculator. Alternatively, measurements and calculations can be made using a digital computer.

Recently, several self-contained devices for measuring defibrillator energy have become commercially available. These devices simply were analog circuit implementations of the calculation equation and they were economically possible when integrated-circuit multipliers became available at reasonable prices which permitted the calculation of $E^2$ in order to calculate the energy.

Other methods of indicating energy output are the use of a resistance network and neon lamp to flash at a predetermined voltage. Many previous attempts at measuring the energy output included a common error which was to misinterpret the energy equation by integrating and then squaring the signal. While this method can be scaled to read energy for a particular waveshape, it is not suitable for any variation from that shape and so is not suitable as a general purpose method.

SUMMARY OF THE INVENTION

The present device is a defibrillator tester and calibrator which measures the output of the defibrillator in true delivered watt seconds (Joules) on a linear scale and indicates polarity and the presence of excessive resistance in leads and internal circuitry of the defibrillator.

The device is portable and requires no power supply inasmuch as the energy is drawn from the defibrillator pulse.

Another advantage of the present device is that it may be used by relatively untrained hospital or repair personnel on a routine basis.

If desired, outputs are provided for the observation of the pulse shape.

Most modern defibrillators in hospital use today are high-voltage, short-pulse D.C. machines usually with line isolated outputs and the Lowne-type output circuit.

Failure or faulty operation of a defibrillator is dangerous particularly as many hospitals rely on a single "crash cart" with no spare defibrillators and the very high currents and voltages involved mean that reliability is difficult to obtain at a low cost.

For example, several faults such as blown fuses, burnt contact on the internal relay, open circuit leads, open circuit transformer, internal wiring faults, open circuit capacitor and the like may cause complete failure of the machine and some of these faults including open patient leads or open capacitor or faulty relays may result in the meter on the defibrillator indicating correct operation whereas in fact the patient is receiving no defibrillator pulse.

Many doctors have the habit of "firing" the defibrillator paddle-to-paddle to make sure there is a spark but this causes very rapid deterioration of the paddles with the associated danger of patient burns.

A more insidious fault for example, a damaged meter or meter resistor, results in low meter readings. The patient is then given a stronger shock that is indicated and the meter on the defibrillator may indicate more energy than is actually reaching the patient due to faulty contacts or high resistance in either the patient leads or internal wiring or to a damaged capacitor.

Almost all defibrillators on the market today have meters calibrated in terms of "stored energy." In actual fact only about 70% of this energy reaches the patient and this percentage varies from manufacturer to manufacturer and depends on the circumstances of actual use.

Basically to test the defibrillator, it is necessary to discharge it into a standard test load such as a 50 ohm load and then measure the power developed. There are of course a number of ways of doing this but these are restricted by the fact that the measuring instrument should be - (a) relatively simple, (b) self powered with no batteries to change or power leads to trip over, and (c) portable.

The principal object and essence of the invention is to provide a device of the character herewithin described in which the voltage or current is measured through a load resistor and the resultant pulse is shaped and stretched and presented on a meter panel.

Another object of the invention is to provide a device of the character herewithin described in which the circuitry uses the energy from the pulse thus eliminating active circuits or batteries.

It should be noted that it is not sufficient to measure the peak voltage as a number of faults may give correct peak voltages but not energy. The power developed by the defibrillator pulse is defined as the integral of the product of voltage and current with respect to time and is indicated by the following formula.

$$\text{Power} = \int_{t=0}^{t=\infty} V \cdot I\, dt = \int_{t=0}^{t=\infty} V^2/R\, dt$$

where R = test load, V = voltage, 1 = current, and $t$ = time after start of the defibrillator pulse.

Conventional instruments usually measure the integral of voltage with respect to time.

$$\int_{t=0}^{t=\infty} V\, dt$$

The scale of the meter is then adjusted to give the square of this value multiplied by the inverse of the resistance.

$$\frac{1}{R}\left[\int_{t=o}^{t=\infty} V\,dt\right]^2$$

but it will be readily appreciated that this is not equal to the power derived from the first equation.

With the foregoing objects in view, and other such objects and advantages as will become apparent to those skilled in the art to which this invention relates as this specification proceeds, my invention consists essentially in the arrangement and construction of parts all as hereinafter more particularly described, reference being had to the accompanying drawings in which:-

FIG. 1 is a schematic wiring diagram of one embodiment of the invention.

FIG. 2 is a schematic wiring diagram of a squarelaw converter.

In the drawings like characters of reference indicate corresponding parts in the different figures.

DETAILED DESCRIPTION

Figure 3:
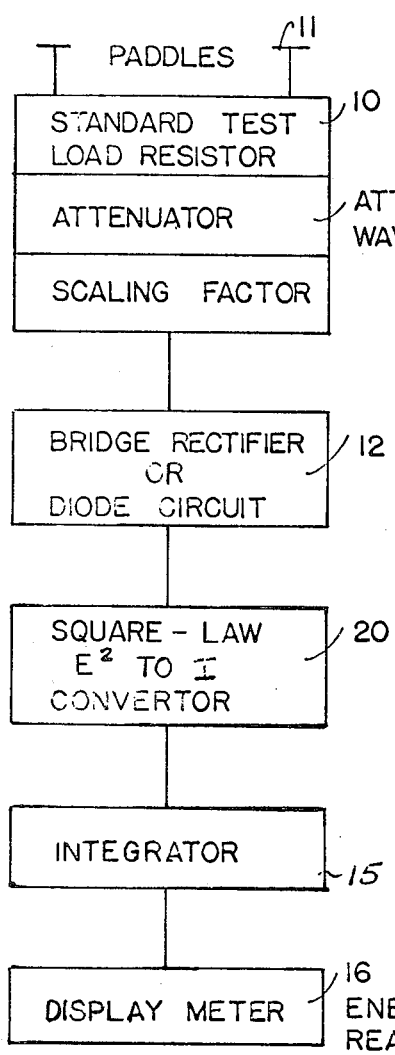
FIG. 3 is a block diagram of the preferred embodiment.

Dealing first with the embodiment shown in FIG. 1, this integrates the current delivered by the defibrillator and presents the average on a meter with a one second time constant. The meter is calibrated in terms of delivered energy (proportional to current). This results in a non-linear scale and a reading which shows the integrated current (or total charge) delivered to the load. This is quite satisfactory clinically although it is not the preferred embodiment.

In FIG. 1, reference character 10 illustrates a standard test load resistor which is adjustable and which is connected to the paddles 11 of the defibrillator being tested.

If a unipolar tester is desired, the diode bridge rectifier 12 is eliminated but if a circuit is required which is responsive to both polarities of input pulse then the bridge rectifier 12 is included as illustrated.

An adjustable potentiometer 13 is included in the output from the bridge rectifier 12, together with a fixed resistance 14.

Capacitor 15 across the leads integrates the current delivered by the defibrillator and presents same on the display meter 16 and this portion of the circuit is classified as the "meter circuit."

The input electrodes 11 are three-inch diameter stainless steel discs insulated from the case of the instrument and the sliding contact on the load 10 is provided for coarse adjustment with fine adjustment being made by the potentionmeter 13.

A standard booster diode filament transformer 17 may be placed across the leads as illustrated and may be used for a test output with the 120 volt primary connected across the tap on the load resistor.

The time constant of the meter 16 is one second giving ample time to read the maximum swing of the needle.

This instrument responds essentially to the integrated charge (current x time) delivered by the defibrillator as follows. Consider the effect of a high resistance fault of, say, 75 ohms in the patient lead. It would be expected that the voltage on the tester would be reduced by half by this fault. This is exactly compensated for by the resultant doubling of the time constant and therefore there would be no change in meter reading. Similarly, a doubling capacitance in the defibrillator in conjunction with a halving of voltage would give an unchanged reading although the stored energy had been reduced by a half. The tester actually gives an indication of stored charge not energy and this is acceptable clinically except in the case of a major equipment fault.

However, this particular embodiment is designed primarily for use a test instrument and is useable for calibration of defibrillators of the Lowne type with short time constants and would not indicate certain types of faults such as high resistance leads, etc. Nor would it indicate the efficiency of various defibrillators in terms of delivered versus stored energy.

Figure 4:
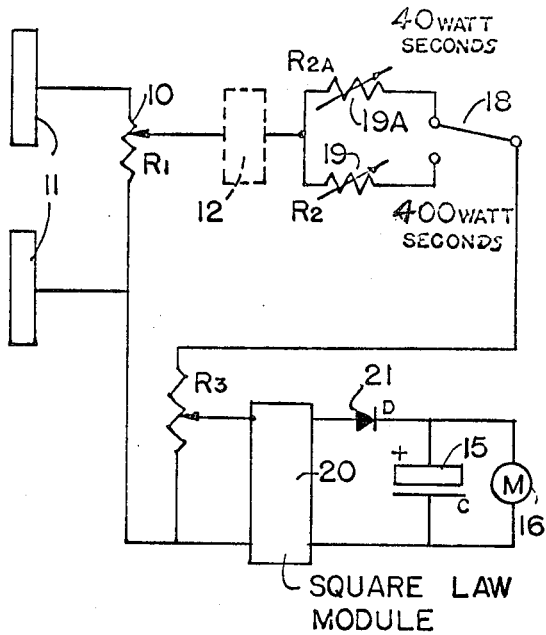
FIG. 4 is a schematic wiring diagram of the preferred embodiment.

In order to measure true delivered energy some sort of power sensitive device is needed and this is illustrated in FIGS. 2, 3 and 4.

A square-law circuit using diodes appear to be one method of obtaining a measurement of the true delivered energy and a typical square-law, voltage to current converter is shown in FIG. 2 and is velieved to be self-explanatory. In this particular example, the diodes are all IN 4446 or 4152. However, it will of course be appreciated that integrated circuitry could be used either hybrid or monolithic.

No adjustment of resistance values is required for good square-law approximation with pulses. When fed from a low impedance source into a low impedance load, this circuit gives a good square-law approximation up to a voltage of 2 + 0.6 N volts, where N equals the number of diodes. Thus $I = KV^2$ ($V\mathrm{max} = 2 + 0.6N$).

The reduction of resistance values from 470 ohms at one end to 82 ohms at the other is due to the need for compensation of the non-ideal diode characteristics.

FIG. 4 shows the preferred circuitry with or without the diode bridge rectifier 12 which is shown schematic form.

A switch 18 is provided routing the pulse through either resistance 19 or resistance 19A. If routed through resistance 19A, the meter 16 is scaled to read 0 to 40 Joules (watt seconds) but if the switch is moved so that the pulse is routed through resistance 19 then the meter is scaled to read between 0 and 400 Joules.

Reference character 20 indicates the voltage to current converter illustrated in FIG. 2.

This generates a current proportional to $E^2$ and then this current is integrated in the capacitor 15 thus indirectly measuring true energy on the meter 16.

As mentioned previously, this differs from standard methods which directly square the voltage to produce a signal proportional to $E^2$.

It will of course be appreciated that the energy output of the defibrillator being tested is dissipated in the resistor $R_1$.

The circuitry described is relatively simple and of course, other variations could be included for integrating and holding the signal proportional to energy but this, of course, would require powered circuitry.

As mentioned in reference to FIG. 1, the attenuated waveform can be connected to an oscilloscope or other device for inspection or recording by the transformer 17.

The germanium diode 21 in FIG. 4, in series with the capacitor 15, serves to lengthen the meter time constant and does not affect accuracy except for very long pulses.

It will therefore be seen that the device measures true delivered watt seconds into a 50 ohm load with a linear meter scale and can be used for the testing and calibrating of defibrillators in the hospital and service shop.

The device can be calibrated using a precision 15 µf capacitor charged to known voltages as a source of known energy.

$$\text{Energy} = \frac{1}{2} \text{capacity} \times (\text{voltage})^2$$

The calibration of the device was further checked under actual use with various defibrillators by photographing the voltage pulse on an oscilloscope, evaluating the integral for energy on a calculator.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as my invention is:

1. A passive defibrillator tester, requiring no manipulation of controls, comprising in combination a standard test load resistor, means operatively connecting said test load resistor to the defibrillator being tested, whereby said defibrillator is discharged into said standard test load resistor, a passive square-law converter, circuit means operatively connecting said standard test load resistor to said converter, and a passive meter circuit operatively connected to said square-law converter, said meter circuit including a passive integrator circuit and a display meter to indicate the true delivered watt seconds input from the defibrillator being tested, into the standard test load resistor, and switch means between said standard test load resistor and said converter, a pair of variable resistors in parallel between said standard test load resistor and said switch means, said switch means placing one variable resistor or the other variable resistor in circuit thereby scaling said meter to one range or another range, said integrator circuit including a diode and capacitor network in said meter circuit.

2. The tester according to claim 1 which includes a bridge rectifier circuit in said tester for making said tester polarity insensitive.

3. The device according to claim 1 in which said standard test load resistor is adjustable within limits, and adjustable potentiometer means in said meter circuit.

4. The device according to claim 2 in which said standard test load resistor is adjustable within limits, and adjustable potentiometer means in said meter circuit.

* * * * *